United States Patent
Whitaker et al.

(10) Patent No.: US 7,951,138 B2
(45) Date of Patent: May 31, 2011

(54) PIVOTING ROLLER TIP FOR DERMATOLOGICAL TREATMENT APPARATUS

(75) Inventors: Kenton Whitaker, Fremont, CA (US); Danica Wyatt, Redwood City, CA (US)

(73) Assignee: Reliant Technologies, LLC, Mountain View, CA (US)

( * ) Notice: Subject to any disclaimer, the term of this patent is extended or adjusted under 35 U.S.C. 154(b) by 309 days.

(21) Appl. No.: 11/936,681

(22) Filed: Nov. 7, 2007

(65) Prior Publication Data

US 2008/0294151 A1     Nov. 27, 2008

Related U.S. Application Data

(60) Provisional application No. 60/939,817, filed on May 23, 2007.

(51) Int. Cl.
*A61B 18/18* (2006.01)

(52) U.S. Cl. .................. 606/9; 606/10; 607/88; 607/89

(58) Field of Classification Search .............. 607/88–94; 606/2–19
See application file for complete search history.

(56) References Cited

U.S. PATENT DOCUMENTS

| | | | |
|---|---|---|---|
| 4,849,859 A * | 7/1989 | Nagasawa | 362/573 |
| 5,346,489 A | 9/1994 | Levy et al. | |
| 5,968,033 A | 10/1999 | Fuller et al. | |
| 6,171,302 B1 * | 1/2001 | Talpalriu et al. | 606/9 |
| 6,306,130 B1 | 10/2001 | Anderson et al. | |
| 6,406,474 B1 * | 6/2002 | Neuberger et al. | 606/9 |
| 6,758,845 B1 * | 7/2004 | Weckwerth et al. | 606/9 |
| 6,926,683 B1 * | 8/2005 | Kochman et al. | 601/118 |
| 2003/0055414 A1 * | 3/2003 | Altshuler et al. | 606/9 |
| 2005/0285928 A1 | 12/2005 | Broome et al. | |
| 2007/0073367 A1 | 3/2007 | Jones et al. | |

OTHER PUBLICATIONS

U.S. Appl. No. 10/745,761, filed Dec. 23, 2003, 33 pages.
PCT International Search Report and Written Opinion, PCT/US07/084165, Apr. 18, 2008, 9 pages.

* cited by examiner

*Primary Examiner* — Ahmed M Farah
(74) *Attorney, Agent, or Firm* — Wood, Herron & Evans, LLP

(57) ABSTRACT

A mechanical element allows the tip of the handpiece of a dermatological treatment system to rotate to adjust for deviations in handpiece angle with respect to the surface of the treatment area. The tip may glide over the surface of the skin, the tip may include wheels or rotating cylinders on which the tip rolls across the skin, or the tip may be removed from the skin and placed in a new location in a stamping motion. The tip of the handpiece rotates around a single axis, or around two perpendicular axes, so that pressure on the tip moves the flat surface of the tip into proper orientation for planar contact with the skin. An element can be included in the handpiece to apply a restoring force on the tip so that the tip rests in its optimal position in the absence of external forces.

6 Claims, 5 Drawing Sheets

FIG. 1A – PRIOR ART

PIVOTING ROLLER TIP FOR DERMATOLOGICAL TREATMENT APPARATUS

CROSS-REFERENCE TO RELATED APPLICATIONS

This application claims priority under 35 U.S.C. §119(e) to U.S. Provisional Patent Application Ser. No. 60/939,817, "Pivoting Roller Tip for Dermatological Treatment Apparatus", filed May 23, 2007, by Kenton Whitaker and Danica Wyatt. The subject matter of all of the foregoing is incorporated herein by reference in its entirety.

BACKGROUND OF THE INVENTION

1. Field of the Invention

This invention relates generally to apparatus and method for energy delivery to dermatological tissue. More particularly, it relates to a systems and methods for delivering light via a handpiece that rolls or glides over skin or is generally moved from one location to another on the skin.

2. Description of the Related Art

Medical and aesthetic dermatological treatments are commonly performed by exposing skin to an appropriate quantity of energy at a wavelength absorbed by some component of the skin tissue. For example, energy can be targeted for selected absorption in blood vessels or hair follicles. Wrinkles, hyperpigmentation and scarring can be reduced by devices that target features of the water absorption spectrum. In some cases, a delivery mechanism that exposes only a fraction of the skin surface to light while sparing surrounding tissue may be preferred to a more aggressive treatment that ablates the full epidermis, because a fractional treatment reduces the risk of infection and better stimulates the wound healing response.

Prior medical laser systems have included mechanisms for controlling energy intensity, pulse duration, and size of treatment zones. Known methods often rely on both automated systems and interactive operator control to deliver an optimal treatment. One approach is to deliver light via a handpiece that gives the operator some degree of spatiotemporal control of exposure. Some handpieces are configured for delivering a fractional light exposure. A number of options exist for creating a pattern of exposure on the skin. Some systems deliver energy in a 2-D pattern that is stamped repeatedly onto the skin to cover the treatment area. Some known handpiece designs contain a single focused laser beam or an array of laser spots that are temporally controlled to produce a desired pattern as the handpiece moves over the skin. A subset of these systems also include a method for imaging the skin passing under the tip to calculate a tip velocity for feedback into a system that adjusts the pulse rate of the laser to accommodate changes in an operator's hand speed.

A common disadvantage of existing handpieces is that their automated control of laser focus, pulse rate and energy relies on the assumption that the operator will hold the handpiece normal to the skin surface. While a trained and conscientious clinician may be capable of approaching this level of precision, it is unreasonable to assume absolute consistency, especially in treatment of contoured regions of a treatment area, such as a face.

The consequences of handpiece misalignment depend on the details of the laser treatment. In a system with a 2-D fractional pattern, tilting the handpiece could distort the treatment pattern and shift the focal point of laser spots. The macroscopic result could be inhomogeneity of treatment with possible skin damage in regions of overexposure. A scanning handpiece with velocity feedback depends on normal orientation of the handpiece to properly track movement. Tilting the handpiece by a large angle could interrupt the delivery of treatment by triggering a safety shut-off in the tracking mechanism. This would result in undertreatment of that region of tissue. Even with a small error in angle, the focus of the laser could shift on both horizontal and vertical axes from its calculated target under the epidermis to some unspecified point outside of the treatment region.

SUMMARY OF THE INVENTION

The present invention overcomes the limitations of the prior art by using a mechanical element that allows the tip of the handpiece of a dermatological treatment system to rotate to adjust for deviations in handpiece angle with respect to the surface of the treatment area. The tip of the handpiece includes a planar element with an exit port for laser light. The tip may also include optical elements for redirecting and focusing the laser. Alternatively or additionally, the tip may deliver a 2-D array of laser beams designed for a stamping application of a fractional pattern. In one embodiment, the tip glides over the surface of the skin. In another embodiment, the tip includes wheels or rotating cylinders on which the tip rolls across the skin.

In one embodiment, the tip of the handpiece rotates around a single axis. In this arrangement, unequal forces on opposite sides of the pivot axis caused when only one side of the tip is in contact with the treatment surface would move the tip until the forces are equalized by the tip making planar contact with the treatment surface on both sides of the pivot axis. In one implementation of the single axis of rotation, the pivot point lies between two roller elements of the tip. In another embodiment, the tip of the handpiece rotates around two perpendicular axes, so that pressure on the tip from any angle moves the flat surface of the tip into proper orientation for planar contact with the skin. In another implementation, a socket joint is used to allow full angular pivoting of the tip.

In various embodiments, an element is included in the handpiece to apply a restoring force on the tip so that the tip rests in its optimal position in the absence of external forces, such as those applied when the tip makes contact with the treatment surface. In one implementation, a plastic segment between the handpiece and tip flexes under pressure to maintain contact between the tip and skin surface, and applies a restoring force on the tip to return the tip to its optimal position when not in contact with the skin surface. In some embodiments, the restoring force is sufficient to provide feedback to the operator to indicate a desired corrective action and/or a desired angle for the operator to adjust a tilt of the handpiece.

Other aspects of the invention include methods corresponding to the devices and systems described above.

BRIEF DESCRIPTION OF THE DRAWINGS

The invention has other advantages and features which will be more readily apparent from the following detailed description of the invention and the appended claims, when taken in conjunction with the accompanying drawings, in which FIG. 1A illustrates a prior art design of a roller tip for a dermatological handpiece.

DETAILED DESCRIPTION OF THE PREFERRED EMBODIMENTS

Figure 1B:
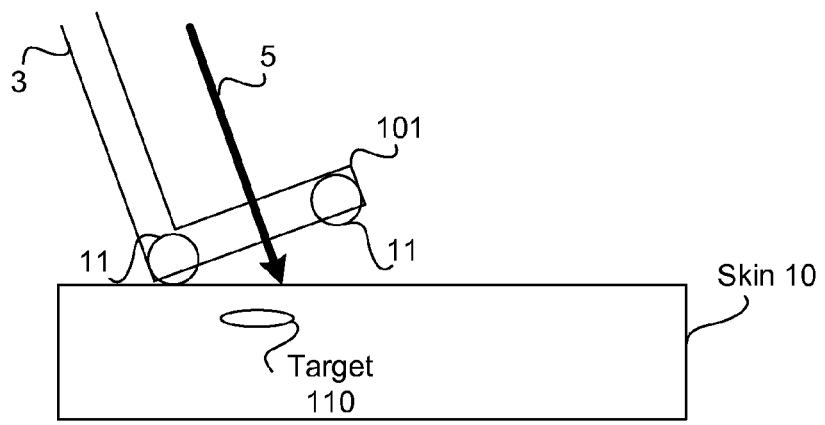
FIGS. 1B and 1C illustrate a pivoting tip for a dermatological handpiece at two different angles with respect to the treatment surface, in accordance with an embodiment of the invention.
Figure 1B:
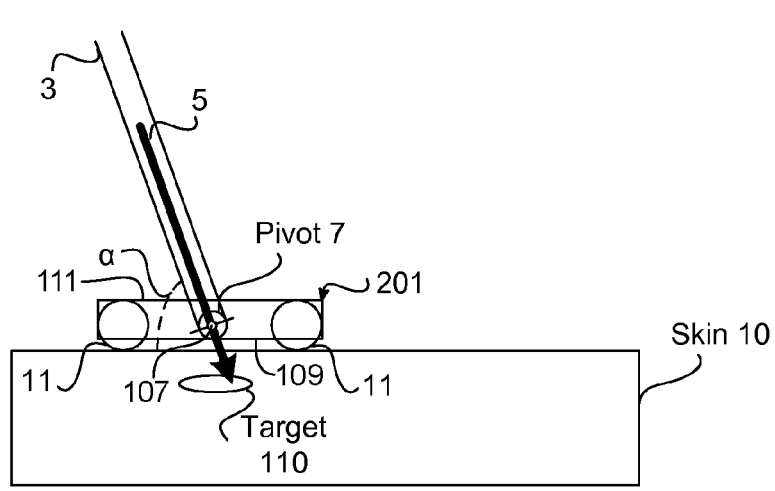

FIG. 1A illustrates a prior art design of a roller tip 101 for a dermatological handpiece. As shown in FIG. 1A, the tip 101 of the dermatological handpiece may become misaligned, i.e., tilted, with respect to the surface of skin 10, and one of the roller elements 11 may lose contact with the skin 10. In some cases, the misalignment is caused by operator error. In other cases, the particular contours of the treatment surface make consistently maintaining the handpiece casing 3 at the proper angle with respect to skin 10 challenging if not impossible as the tip 101 is rolled over the skin 10. As a result, the treatment energy 5 is likely to miss the target 110 of the treatment. In the example shown in FIG. 1A, the tilt of the tip causes the treatment energy 5 to fail to penetrate the skin to the appropriate depth, and the target 110 is under-exposed as a consequence.

Figure 1C:
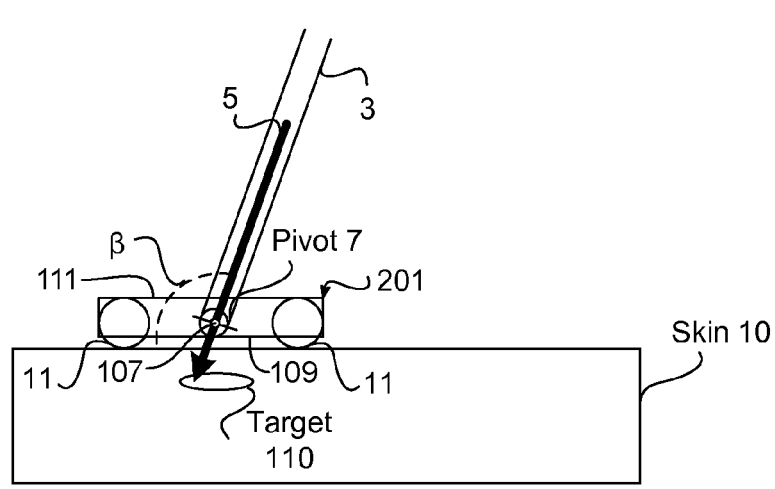

FIGS. 1B and 1C illustrate a pivoting roller tip 201 for a dermatological handpiece at two different angles with respect to the treatment surface, in accordance with one embodiment of the invention. In one implementation of the single axis of rotation, the pivot point 7 lies between two roller elements 11 of the tip. Roller elements 11 may be wheels or rotating cylinders, for example. In this arrangement, unequal forces on opposite sides of the pivot axis caused when only one side of the tip 201 or one of the roller elements 11 is in contact with the treatment surface would rotate the tip 201 until the forces are equalized by the tip 201 or the roller elements 11 making contact with the treatment surface on both sides of the pivot mechanism 7. As shown in FIG. 1B, the tip 201 of the dermatological handpiece maintains proper alignment and roller elements 11 maintain contact with the surface of skin 10, despite the handpiece casing 3 being held such that treatment energy 5 is incident on skin at an acute angle α. In FIG. 1C, the tip 201 maintains proper alignment and roller elements 11 maintain contact with the surface of skin, when the handpiece casing 3 is held such that the treatment energy 5 is incident on the skin at an obtuse angle β as well. In both examples, the pivot mechanism 7 allows the tip 201 to rotate along one axis with respect to the handpiece casing 3, and the treatment energy 5 hits the target 110.

It is particularly beneficial for the roller elements 11 to maintain contact with the surface of the skin 10 in devices wherein feedback is provided based on the velocity or positional parameters of one or more roller elements 11. For example, such feedback can be to the user to indicate that the user is moving too fast or too slow or can be to a laser controller for control of the pulse energy, pulse repetition rate, and/or pulse timing. Examples of systems employing such a feedback system are described in additional detail in copending U.S. patent application Ser. No. 11/744,161, entitled "Opto-mechanical apparatus and method for dermatological treatment," which is herein incorporated by reference.

FIGS. 1B and 1C illustrate a pivoting roller tip 201 for a dermatological handpiece at two different angles with respect to the treatment surface, in accordance with one embodiment of the invention. In one implementation of the single axis 107 of rotation, the pivot point 7 lies between two roller elements 11 of the tip. Roller elements 11 may be wheels or rotating cylinders, for example. In this arrangement, unequal forces on opposite sides of the pivot axis 107 used when only one side of the tip 201 or one of the roller elements 11 is in contact with the treatment surface would rotate the tip 201 until the forces are equalized by the tip 201 or the roller elements 11 making contact with the treatment surface on both sides of the pivot mechanism 7. As shown in FIG. 1B, the tip 201 of the dermatological handpiece maintains proper alignment and roller elements 11 maintain contact with the surface of skin 10, despite the handpiece casing 3 being held such that treatment energy 5 is incident on skin at an acute angle α. In FIG. 1C, the tip 201 maintains proper alignment and roller elements 11 maintain contact with the surface of skin, when the handpiece casing 3 is held such that the treatment energy 5 is incident on the skin at an obtuse angle β as well. In both examples, the pivot mechanism 7 allows the tip 201 to rotate along one axis 107 with respect to the handpiece casing 3, and the treatment energy 5 hits the target 110. The tip 201 of the dermatological handpiece rotates around the single axis 107 so that pressure on the tip 201 moves a flat surface 109 of a planar element 111 of the tip 201 into proper orientation for planar contact with the skin 10.

Figure 3A:
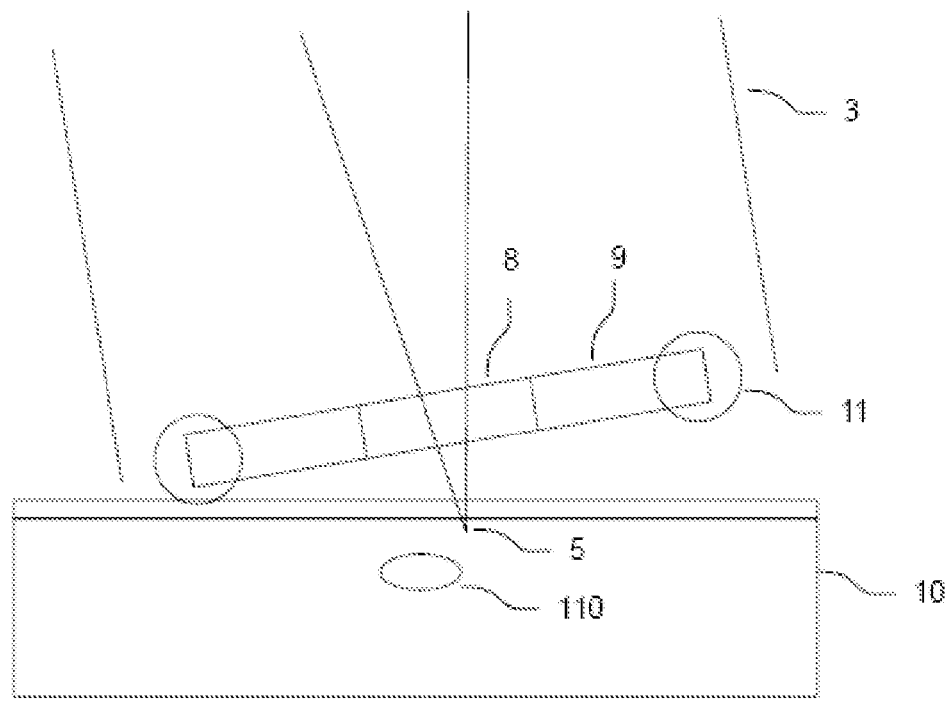
FIG. 3A illustrates an example shift in focal point of a laser that occurs when a handpiece with a rolling tip is misaligned with the treatment surface.
Figure 3B:
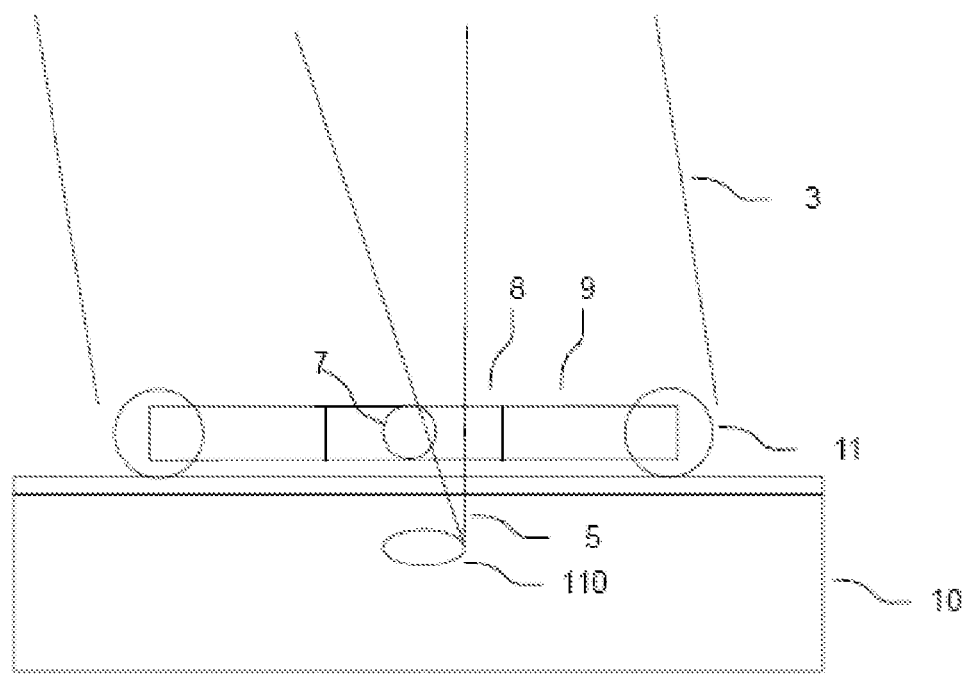
FIG. 3B illustrates a single axis pivoting tip for improving laser aim, in accordance with one embodiment.

FIG. 3A illustrates an example shift in focal point of a laser that occurs when a handpiece with a rolling tip is misaligned with the treatment surface. As shown in FIG. 3A, a handpiece having a tip 9 rigidly attached to the handpiece casing 3 is tilted with respect to the surface of skin 10. This results in the focal point of treatment energy 5 missing the treatment target 110. In contrast, FIG. 3B illustrates a single axis pivoting tip for improving laser aim, in accordance with one embodiment. The pivoting action allows the tip 9 to stay in contact with the skin 10 even if the angle of the handpiece with respect to the surface of the treatment area deviates from normal. Thus, the treatment energy 5 is focused at the target 110.

In one implementation, locating the pivot axis 7 close to the treatment area is advantageous in that the optical path length of the beams is preserved such that the beams are approximately the right size as they enter the skin 10. This prevents problems caused by having optical path lengths change when the handpiece is tilted, such as the adjacent beams overlapping or the beam size altering, which can cause under or over-exposure. In other embodiments, the pivot axis 7 can be located below the skin 10 surface at the beam focal point or can be adjusted to other locations depending on the desired optical effect, such as to compensate for the change in angle and preserve the beam cross-sectional area on the skin surface or at some desired level within the skin, such as the dermal-epidermal junction.

FIG. 3A illustrates an example shift in focal point of a laser that occurs when a handpiece with a rolling tip is misaligned with the treatment surface. The treatment energy 5 passes through a transparent window 8 of tip 9 to reach the skin 10. The transparent window 8 defines an exit port in the planar element 111 of the rolling tip for the treatment energy 5. As shown in FIG. 3A, a handpiece having a tip 9 rigidly attached to the handpiece casing 3 is tilted with respect to the surface of skin 10. This results in the focal point of treatment energy 5 missing the treatment target 110. In contrast, FIG. 3B illustrates a single axis pivoting tip for improving laser aim, in accordance with one embodiment. The pivoting action allows the tip 9 to stay in contact with the skin 10 even if the angle of the handpiece with respect to the surface of the treatment area deviates from normal. Thus, the treatment energy 5 is focused at the target 110. Alternative embodiments can employ springs, rubber stretching members, flexible compression members, or other means for generating a restorative force.

In some embodiments, the restoring force is sufficient to provide feedback to the operator to indicate a desired corrective action and/or a desired angle for the operator to adjust a tilt of the handpiece. For example, the restoring force can give an operator feedback on how far the operator was tilting the handpiece from normal, such that the operator can correct the misalignment of the handpiece. This can improve the delivery of the treatment beam(s) to the desired treatment location(s).

Figure 5:
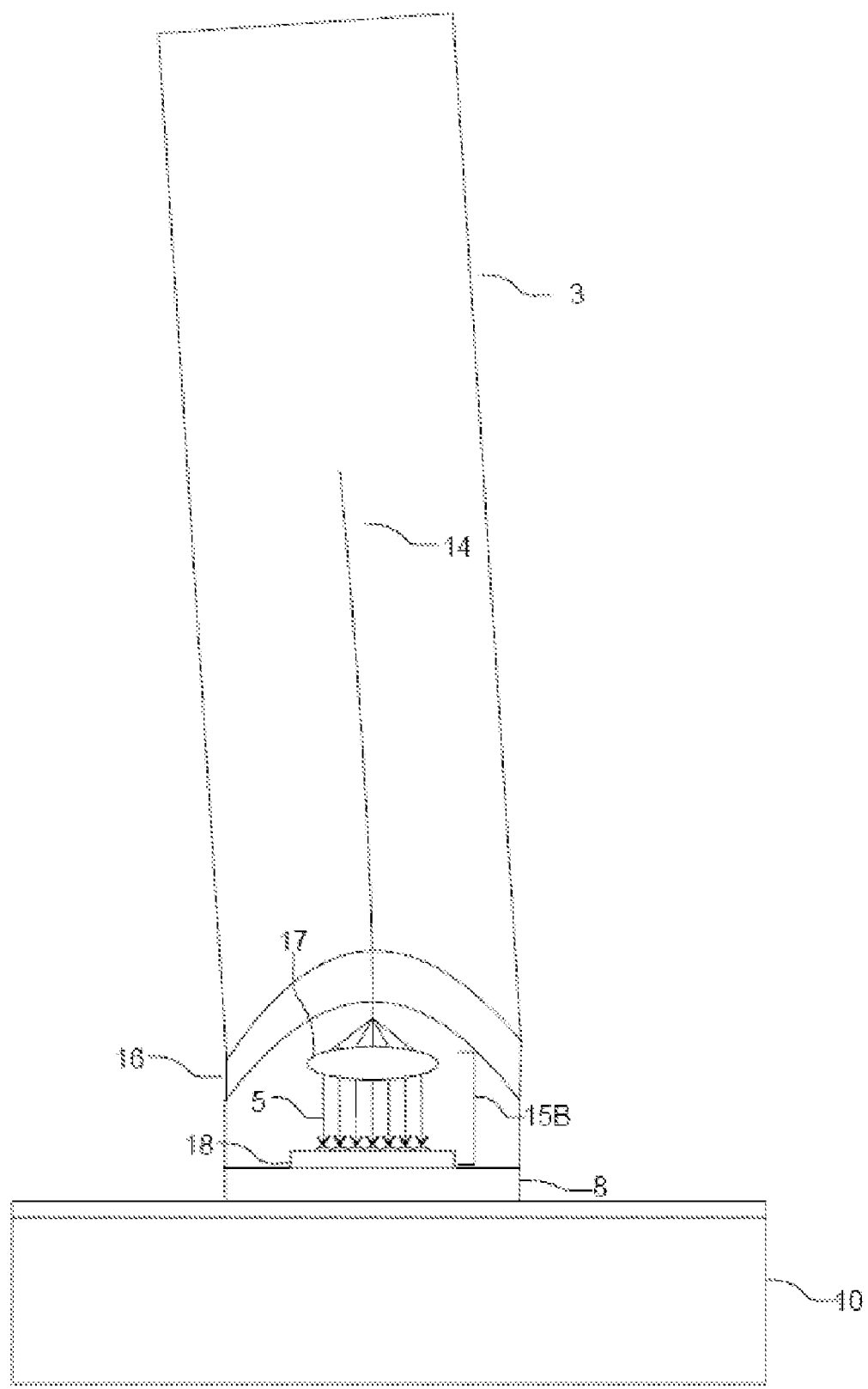
FIG. 5 illustrates a configuration for a 2-D beam array delivery with a tip and handpiece joined by a compressible medium, in accordance with one embodiment.

FIG. 5 illustrates a configuration for a 2-D array delivery with a tip and handpiece joined by a compressible medium 16, in accordance with one embodiment. In this embodiment, the handpiece casing 3 houses an optical fiber 14 that carries laser light to delivery optics 15B that deliver the treatment energy 5 according to a desired 2-D treatment pattern. In the embodiment depicted in FIG. 5, the delivery optics comprises a collimating lens 17 and a lens array 18. Other embodiments will be evident to those skilled in the art. The treatment energy 5 in the 2-D pattern passes through transparent window 8 to the treatment area. In the embodiment shown in FIG. 5, a compressible medium 16, such as a compressible plastic, is placed between the handpiece and the tip. The compressible medium asserts a restorative force on the tip so that the tip rests in its optimal position in the absence of external forces, such as the forces applied when the tip makes contact with the treatment surface. However, the compressible medium 16 between the handpiece and tip flexes under pressure to maintain contact between the tip and skin surface as the tip glides along the contours of the skin surface. 1-D and 3-D treatment patterns can also be used, as desired.

Although the detailed description contains many specifics, these should not be construed as limiting the scope of the invention but merely as illustrating different examples and aspects of the invention. It should be appreciated that the scope of the invention includes other embodiments not discussed in detail above. The aspects of this invention as described above can be further combined to create other embodiments that are within the scope of this invention.

Various other modifications, changes and variations which will be apparent to those skilled in the art may be made in the arrangement, operation and details of the method and apparatus of the present invention disclosed herein without departing from the spirit and scope of the invention.

What is claimed is:

1. An apparatus for use with a treatment energy source in a dermatological treatment, the apparatus comprising:
    a handpiece including a handpiece casing; and
    a pivoting tip connected to the handpiece casing by a pivot axis, the pivoting tip including a planar element with a flat surface and an exit port on the flat surface for the treatment energy, a first roller element coupled with the planar element, and a second roller element coupled with the planar element, the planar element configured to receive treatment energy from the treatment energy source and to deliver the treatment energy from the exit port to a target region of the skin, the pivot axis located between the first roller element and the second roller element, the planar element configured to roll on the first roller element and the second roller element across a surface of the target region of skin, and the planar element configured to pivot relative to the handpiece casing about the pivot axis for adjusting to deviations in handpiece angle with respect to the surface of the target region of skin so that a portion of the pivoting tip maintains contact with the surface of the target region of skin.

2. The apparatus of claim 1 further comprising:
    an illumination lens housed inside the handpiece casing, the illumination lens directing the treatment energy from the treatment energy source to the planar element.

3. The apparatus of claim 1 wherein the handpiece casing is configured to direct the treatment energy from the treatment energy source to the planar element.

4. The apparatus of claim 1 wherein the pivoting tip is selectively removable from the handpiece housing.

5. The apparatus of claim 1 wherein the first roller element and the second roller element are the portion of the pivoting tip maintaining contact with the surface of the target region of skin.

6. The apparatus of claim 1 wherein the flat surface of the planar element is the portion of the pivoting tip maintaining contact with the surface of the target region of skin.

* * * * *

UNITED STATES PATENT AND TRADEMARK OFFICE
CERTIFICATE OF CORRECTION

| | | |
|---|---|---|
| PATENT NO. | : 7,951,138 B2 | Page 1 of 3 |
| APPLICATION NO. | : 11/936681 | |
| DATED | : May 31, 2011 | |
| INVENTOR(S) | : Kenton Whitaker et al. | |

It is certified that error appears in the above-identified patent and that said Letters Patent is hereby corrected as shown below:

At column 1, line number 20, change "to a systems" to --to systems-- and at line number 50, change "include" to --includes--.

At column 3, line numbers 34-57, change "FIGS. 1B and 1C illustrate a pivoting roller tip 201 for a dermatological handpiece at two different angles with respect to the treatment surface, in accordance with one embodiment of the invention. In one implementation of the single axis of rotation, the pivot point 7 lies between two roller elements 11 of the tip. Roller elements 11 may be wheels or rotating cylinders, for example. In this arrangement, unequal forces on opposite sides of the pivot axis caused when only one side of the tip 201 or one of the roller elements 11 is in contact with the treatment surface would rotate the tip 201 until the forces are equalized by the tip 201 or the roller elements 11 making contact with the treatment surface on both sides of the pivot mechanism 7. As shown in FIG. 1B, the tip 201 of the dermatological handpiece maintains proper alignment and roller elements 11 maintain contact with the surface of skin 10, despite the handpiece casing 3 being held such that treatment energy 5 is incident on skin at an acute angle α. In FIG. 1C, the tip 201 maintains proper alignment and roller elements 11 maintain contact with the surface of skin, when the handpiece casing 3 is held such that the treatment energy 5 is incident on the skin at an obtuse angle β as well. In both examples, the pivot mechanism 7 allows the tip 201 to rotate along one axis with respect to the handpiece casing 3, and the treatment energy 5 hits the target 110." to --FIGS. 1B and 1C illustrate a pivoting roller tip 201 for a dermatological handpiece at two different angles with respect to the treatment surface, in accordance with one embodiment of the invention. In one implementation of the single axis 107 of rotation, the pivot point 7 lies between two roller elements 11 of the tip. Roller elements 11 may be wheels or rotating cylinders, for example. In this arrangement, unequal forces on opposite sides of the pivot axis 107 used when only one side of the tip 201 or one of the roller elements 11 is in contact with the treatment surface would rotate the tip 201 until the forces are equalized by the tip 201 or the roller elements 11 make contact with the treatment surface on both sides of the pivot mechanism 7. As shown in FIG. 1B, the tip 201 of the dermatological handpiece maintains proper alignment and roller elements 11 maintain contact with the surface of skin 10, despite the handpiece casing 3 being held such that treatment energy 5 is incident on skin at an acute angle α. In FIG. 1C, the tip 201 maintains proper alignment and roller Signed and Sealed this
Twenty-sixth Day of July, 2011

David J. Kappos
*Director of the United States Patent and Trademark Office* elements 11 maintain contact with the surface of skin, when the handpiece casing 3 is held such that the treatment energy 5 is incident on the skin at an obtuse angle β as well. In both examples, the pivot mechanism 7 allows the tip 201 to rotate along one axis 107 with respect to the handpiece casing 3, and the treatment energy 5 hits the target 110. The tip 201 of the dermatological handpiece rotates around the single axis 107 so that pressure on the tip 201 moves a flat surface 109 of a planar element 111 of the tip 201 into proper orientation for planar contact with the skin 10.-- as set forth in the February 26, 2010 Amendment to Specification.

Figure 2:
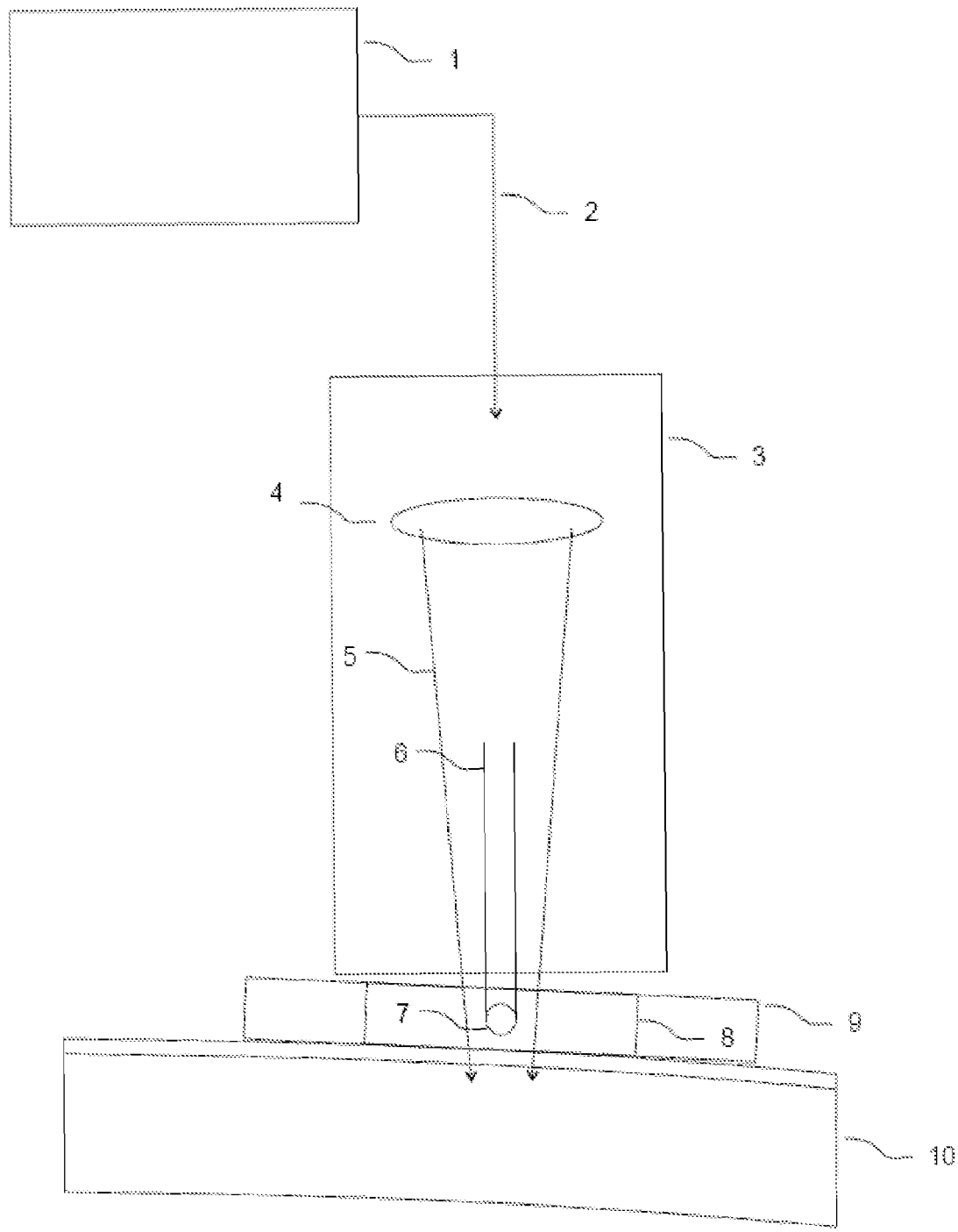
FIG. 2 is a diagram of a full handpiece showing the pivot point of the tip, in accordance with one embodiment.

At column 4, line numbers 2-30, change "FIGS. 1B and 1C illustrate a pivoting roller tip 201 for a dermatological handpiece at two different angles with respect to the treatment surface, in accordance with one embodiment of the invention. In one implementation of the single axis 107 of rotation, the pivot point 7 lies between two roller elements 11 of the tip. Roller elements 11 may be wheels or rotating cylinders, for example. In this arrangement, unequal forces on opposite sides of the pivot axis 107 used when only one side of the tip 201 or one of the roller elements 11 is in contact with the treatment surface would rotate the tip 201 until the forces are equalized by the tip 201 or the roller elements 11 making contact with the treatment surface on both sides of the pivot mechanism 7. As shown in FIG. 1B, the tip 201 of the dermatological handpiece maintains proper alignment and roller elements 11 maintain contact with the surface of skin 10, despite the handpiece casing 3 being held such that treatment energy 5 is incident on skin at an acute angle α. In FIG. 1C, the tip 201 maintains proper alignment and roller elements 11 maintain contact with the surface of skin, when the handpiece casing 3 is held such that the treatment energy 5 is incident on the skin at an obtuse angle β as well. In both examples, the pivot mechanism 7 allows the tip 201 to rotate along one axis 107 with respect to the handpiece casing 3, and the treatment energy 5 hits the target 110. The tip 201 of the dermatological handpiece rotates around the single axis 107 so that pressure on the tip 201 moves a flat surface 109 of a planar element 111 of the tip 201 into proper orientation for planar contact with the skin 10." to --FIG, 2 is a diagram of a full handpiece of the dermatological treatment apparatus showing the pivot point 7 of a removable tip 9, in accordance with one embodiment. The dermatological treatment apparatus includes a treatment energy source 1, which is coupled to the handpiece through an optical and control coupling 2. The handpiece comprises a handpiece casing 3, which houses an illumination lens 4 that directs treatment energy 5 from the treatment energy source 1 toward the skin 10. In the embodiment shown in FIG. 2, the handpiece includes a removable tip 9 that pivots around pivot point 7. In this example, the removable tip 9 glides across the surface of the skin 10. The removable tip 9 is anchored to the handpiece casing 3 at anchor point 6. The treatment energy 5 passes through a transparent window 8 of removable tip 9 to reach the treatment area of skin 10. As shown in FIG. 2, the removable tip 9 has tilted slightly to accommodate a curve in the surface of skin 10. Thus, the majority of the surface of the tip 9 remains in contact with the surface of the skin 10, despite the angle of the handpiece casing 3 with respect to the skin 10. -- as appears in paragraph 22 of the specification as filed November 7, 2007.

At column 4, line numbers 31-42, change "FIG. 3A illustrates an example shift in focal point of a laser that occurs when a handpiece with a rolling tip is misaligned with the treatment surface. As shown in FIG. 3A, a handpiece having a tip 9 rigidly attached to the handpiece casing 3 is tilted with respect to the surface of skin 10. This results in the focal point of treatment energy 5 missing the treatment target 110. In contrast, FIG. 3B illustrates a single axis pivoting tip for improving laser aim, in accordance with one embodiment. The pivoting action allows the tip 9 to stay in contact with the

CERTIFICATE OF CORRECTION (continued)
U.S. Pat. No. 7,951,138 B2 skin 10 even if the angle of the handpiece with respect to the surface of the treatment area deviates from normal. Thus, the treatment energy 5 is focused at the target 110." to --FIG. 3A illustrates an example shift in focal point of a laser that occurs when a handpiece with a rolling tip is misaligned with the treatment surface. The treatment energy 5 passes through a transparent window 8 of tip 9 to reach the skin 10. The transparent window 8 defines an exit port in the planar element 111 of the rolling tip for the treatment energy 5. As shown in FIG. 3A, a handpiece having a tip 9 rigidly attached to the handpiece casing 3 is tilted with respect to the surface of skin 10. This results in the focal point of treatment energy 5 missing the treatment target 110. In contrast, FIG. 3B illustrates a single axis pivoting tip for improving laser aim, in accordance with one embodiment. The pivoting action allows the tip 9 to stay in contact with the skin 10 even if the angle of the handpiece with respect to the surface of the treatment area deviates from normal. Thus, the treatment energy 5 is focused at the target 110.-- as appears in February 26, 2010 amendment to specification.

Figure 4:
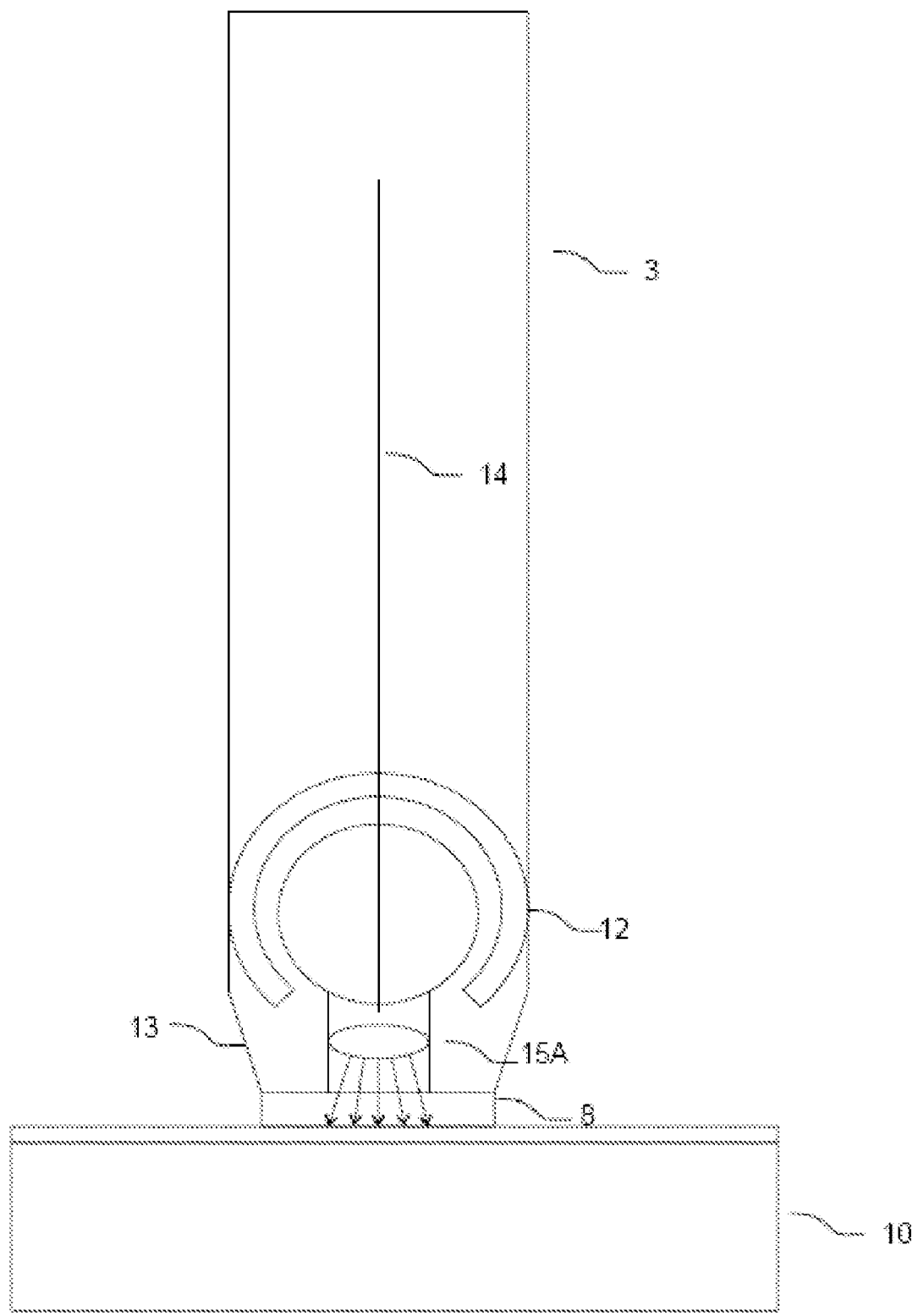
FIG. 4 illustrates a tip with rotation on two perpendicular axes and fiber delivery of laser light to the skin, in accordance with one embodiment.

At column 4, line number 57 through column 5, line number 7, change "FIG. 3A illustrates an example shift in focal point of a laser that occurs when a handpiece with a rolling tip is misaligned with the treatment surface. The treatment energy 5 passes through a transparent window 8 of tip 9 to reach the skin 10. The transparent window 8 defines an exit port in the planar element 111 of the rolling tip for the treatment energy 5. As shown in FIG. 3A, a handpiece having a tip 9 rigidly attached to the handpiece casing 3 is tilted with respect to the surface of skin 10. This results in the focal point of treatment energy 5 missing the treatment target 110. In contrast, FIG. 3B illustrates a single axis pivoting tip for improving laser aim, in accordance with one embodiment. The pivoting action allows the tip 9 to stay in contact with the skin 10 even if the angle of the handpiece with respect to the surface of the treatment area deviates from normal. Thus, the treatment energy 5 is focused at the target 110. Alternative embodiments can employ springs, rubber stretching members, flexible compression members, or other means for generating a restorative force." to --FIG. 4 illustrates a tip with rotation on two perpendicular axes and an optical fiber 14 for delivery of laser light to the skin, in accordance with one embodiment. In the example shown in FIG. 4, the handpiece casing 3 houses an optical fiber 14 carrying the laser light, which is delivered to the skin through delivery optics 15A, which may comprise one or more optical elements and an optical scanner. As in the examples discussed above, the light passes through transparent window 8 of the tip to the treatment area. In this example, the handpiece casing 3 also houses a socket joint 12 that allows full angular pivoting of the tip. In this embodiment, the handpiece casing 3 is attached to a flexible membrane 13 that surrounds the socket joint and attaches to the window 8 of the tip. In one implementation, the flexible membrane 13 asserts a restorative force on the tip so that the tip rests in its optimal position in the absence of external forces, such as the forces applied when the tip makes contact with the treatment surface. Alternative embodiments can employ springs, rubber stretching members, flexible compression members, or other means for generating a restorative force.-- as appears in the specification as filed November 7, 2007.

At column 5, line number 23, change "comprises" to --comprise--.